US010094844B2

(12) United States Patent
Saito et al.

(10) Patent No.: US 10,094,844 B2
(45) Date of Patent: Oct. 9, 2018

(54) AUTOMATIC ANALYZER

(75) Inventors: Yoshiaki Saito, Tokyo (JP); Kazuhiro Nakamura, Tokyo (JP); Naoto Suzuki, Tokyo (JP); Toshihide Orihashi, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 256 days.

(21) Appl. No.: 14/236,659

(22) PCT Filed: Jun. 29, 2012

(86) PCT No.: PCT/JP2012/066637
§ 371 (c)(1),
(2), (4) Date: Feb. 3, 2014

(87) PCT Pub. No.: WO2013/035418
PCT Pub. Date: Mar. 14, 2013

(65) Prior Publication Data
US 2014/0170023 A1    Jun. 19, 2014

(30) Foreign Application Priority Data
Sep. 5, 2011 (JP) ................................. 2011-192261

(51) Int. Cl.
*G01N 35/04*    (2006.01)
*G01N 35/00*    (2006.01)
*G01N 35/02*    (2006.01)

(52) U.S. Cl.
CPC ......... *G01N 35/04* (2013.01); *G01N 35/0095* (2013.01); *G01N 35/026* (2013.01);
(Continued)

(58) Field of Classification Search
None
See application file for complete search history.

(56) References Cited

U.S. PATENT DOCUMENTS 6,080,364 A    6/2000 Mimura et al.
6,261,521 B1 *  7/2001 Mimura ................. G01N 35/04
                                                422/63
(Continued)

FOREIGN PATENT DOCUMENTS

JP    11-064342 A     3/1999
JP    2000-088860 A * 3/2000
(Continued)

OTHER PUBLICATIONS

Japanese Office Action received in corresponding Japanese Application No. 2013-532483 dated Jan. 6, 2015.

*Primary Examiner* — Benjamin R Whatley
(74) *Attorney, Agent, or Firm* — Mattingly & Malur, PC

(57) ABSTRACT

In determining whether a rack inputted to the automatic analyzer by the user is to be transferred to an analysis section or not, samples existing in a route from a buffer to a sample dispensing position in the analysis section are identified, and the number of items in which suction by a nozzle has not been completed in analysis items requested for the samples is managed. When the number of items is reduced to be smaller than a given number, the conveyance of a next rack from the buffer to the analysis section is controlled, thereby limiting the number of analysis items requested for samples in a waiting state for analysis in the analysis section constantly to be smaller than a fixed number. As a result, a period of time until a measurement result of emergency samples is outputted can be reduced even when emergency samples are newly inputted.

4 Claims, 5 Drawing Sheets

(52) U.S. Cl.
CPC ............... *G01N 2035/0415* (2013.01); *G01N 2035/0462* (2013.01)

(56) References Cited

U.S. PATENT DOCUMENTS

| | | | |
|---|---|---|---|
| 6,444,171 B1 * | 9/2002 | Sakazume | G01N 35/0095 422/65 |
| 2004/0186360 A1 * | 9/2004 | Suzuki | G01N 35/026 600/310 |
| 2009/0162247 A1 * | 6/2009 | Tokieda | G01N 35/026 422/65 |
| 2011/0259129 A1 * | 10/2011 | Murata | G01N 35/00693 73/866.3 |
| 2011/0271773 A1 * | 11/2011 | Komatsu | G01N 35/0092 73/863.01 |
| 2012/0294765 A1 * | 11/2012 | Watabe | G01N 35/0092 422/65 |

FOREIGN PATENT DOCUMENTS

| | | | | |
|---|---|---|---|---|
| JP | 2000-088860 A | 3/2000 | | |
| JP | 2002-357612 A | 12/2002 | | |
| JP | 2003-177136 A | 6/2003 | | |
| JP | 3760800 B2 | 1/2006 | | |
| JP | 2006-343351 A | 12/2006 | | |
| JP | 2010-181197 A | 8/2010 | | |
| JP | WO 2010087303 A1 * | 8/2010 | ......... | G01N 35/0092 |
| WO | 2011/093442 A1 | 8/2011 | | |
| WO | WO-2011093442 A1 * | 8/2011 | ......... | G01N 35/0092 |

\* cited by examiner

[FIG. 1]
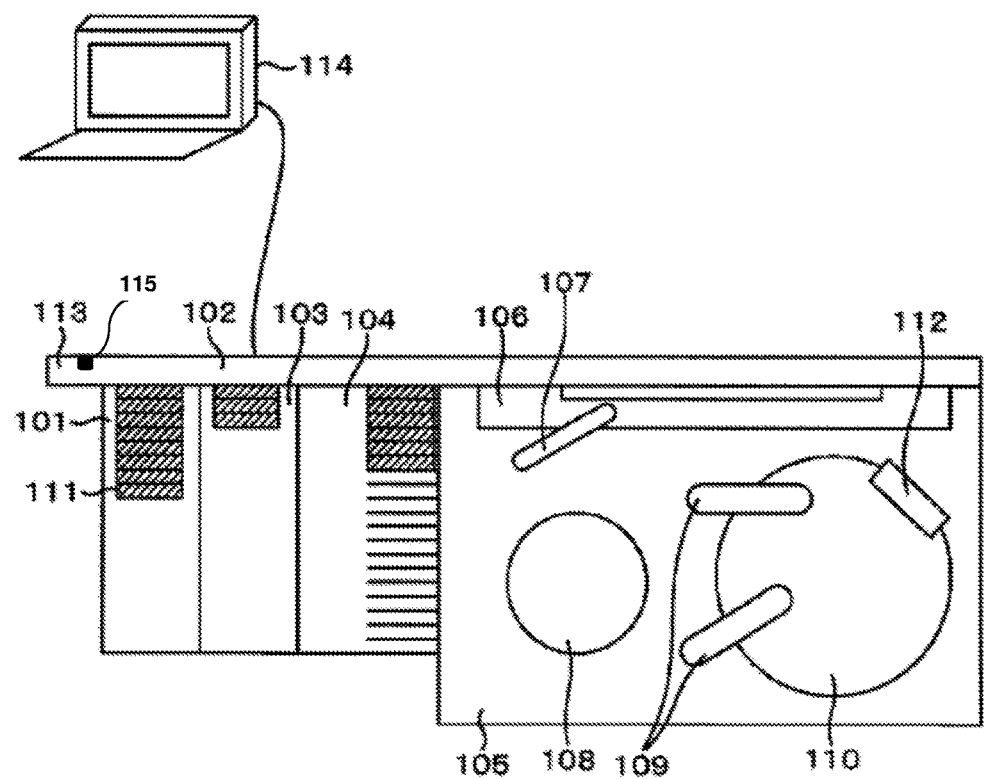

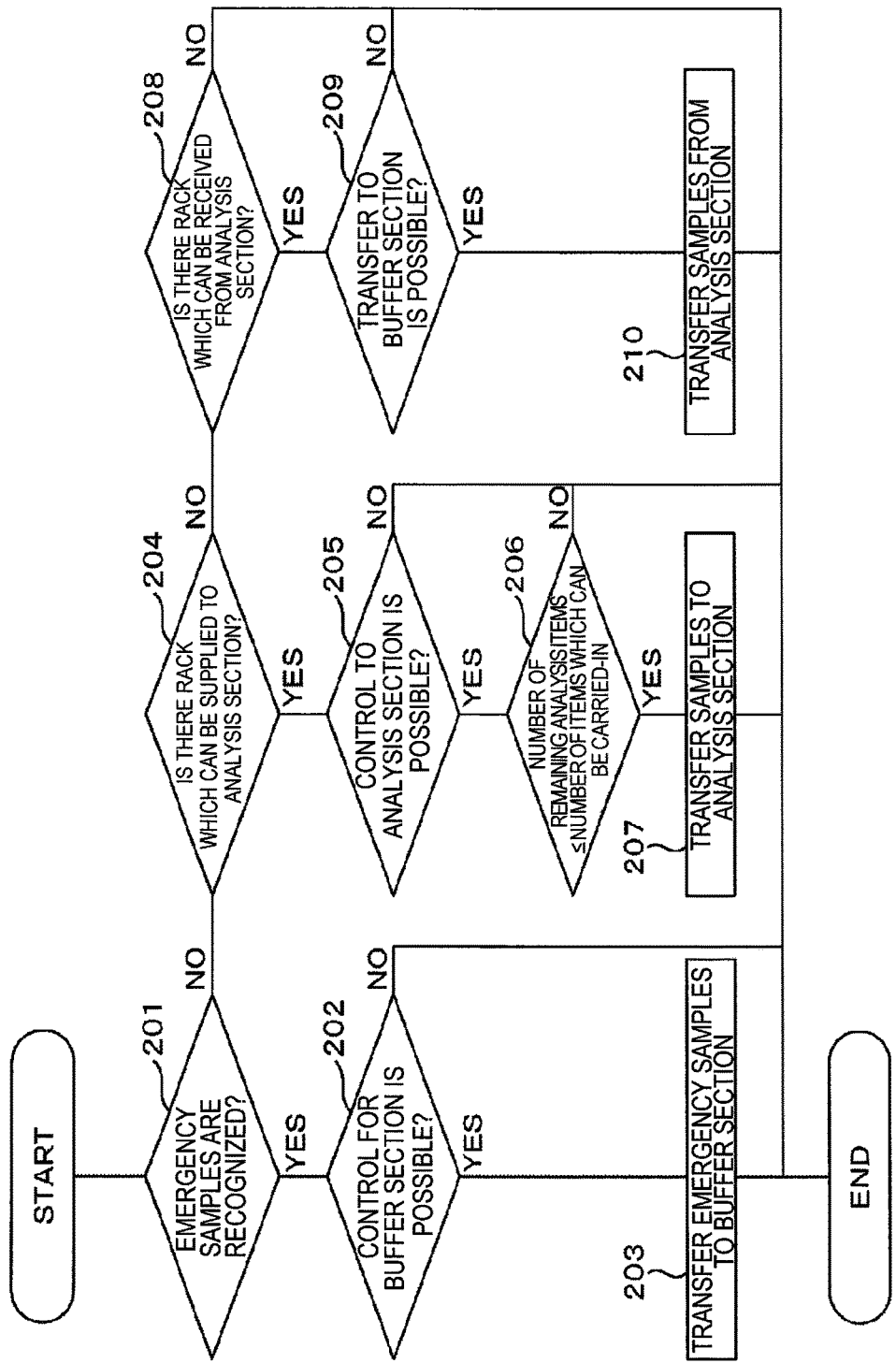
[FIG. 2]

[FIG. 3]
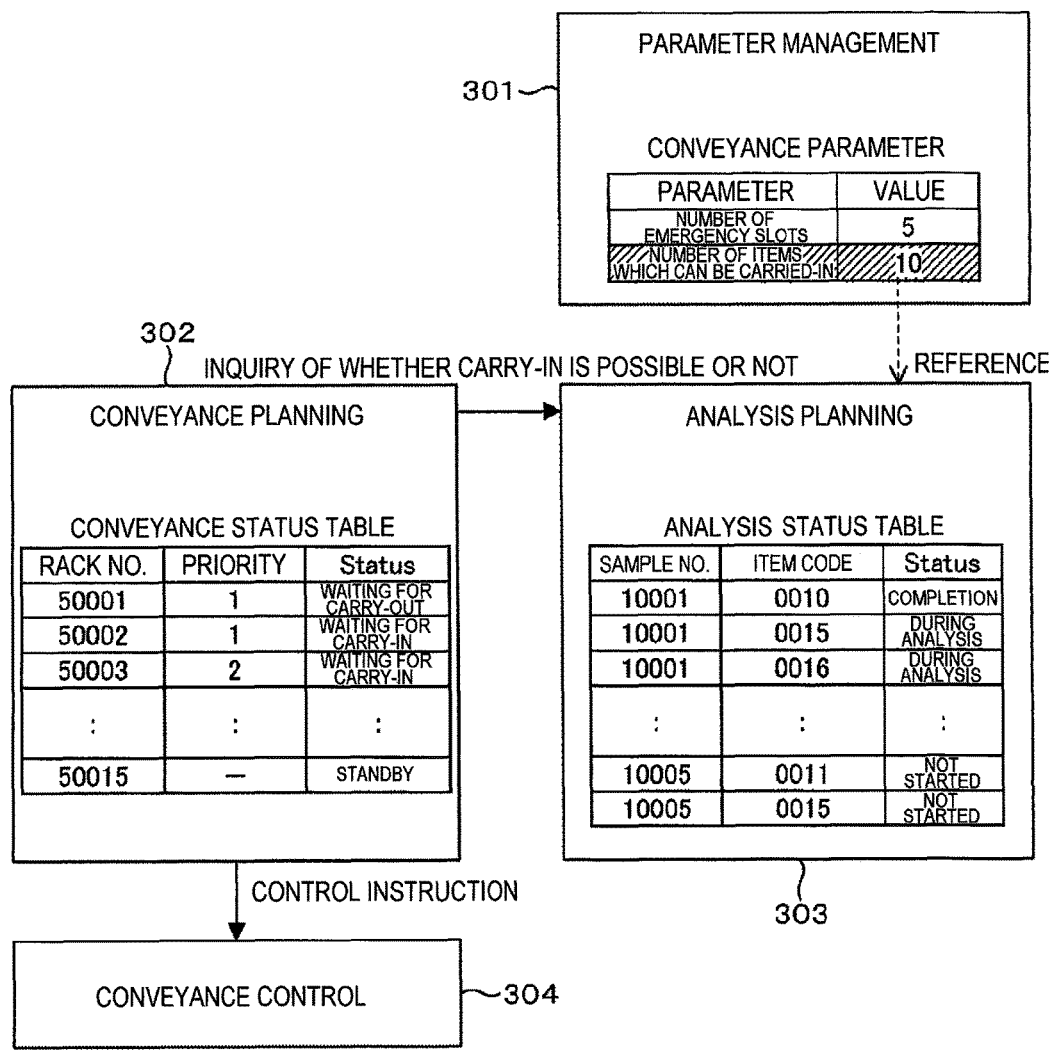

[FIG. 4]
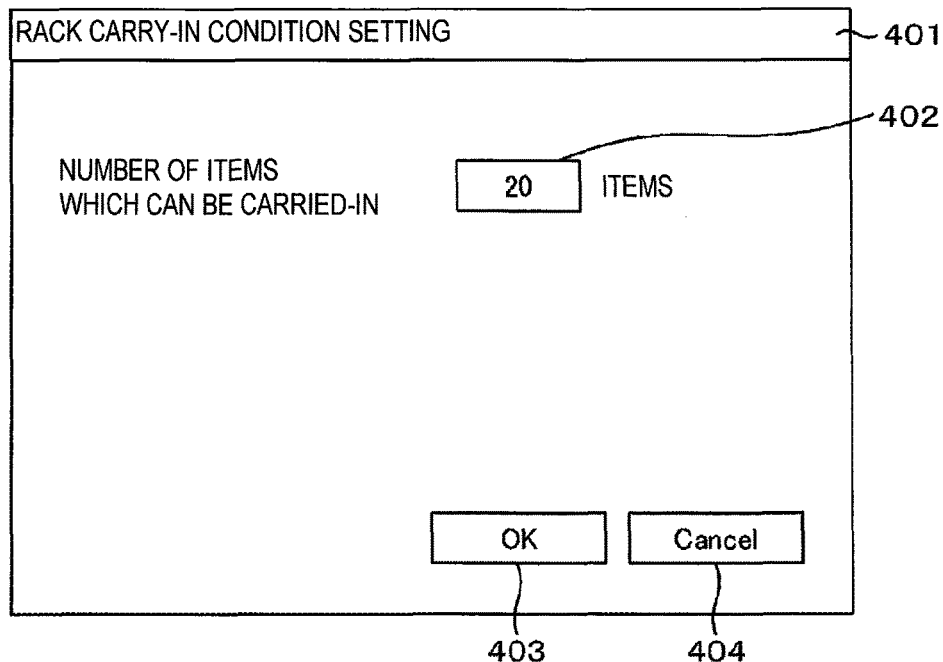
[FIG. 5]
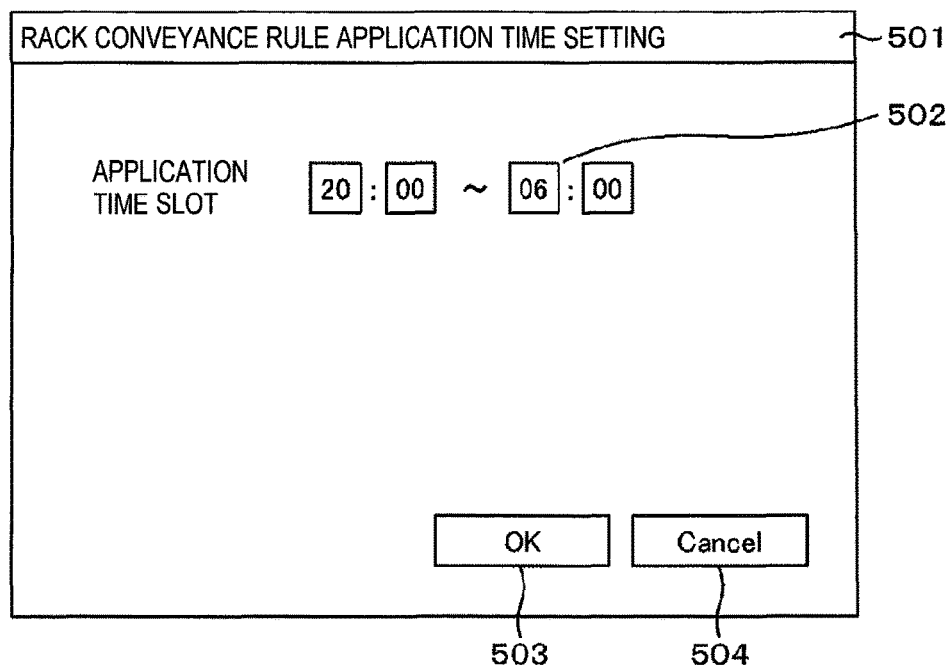

[FIG. 6]
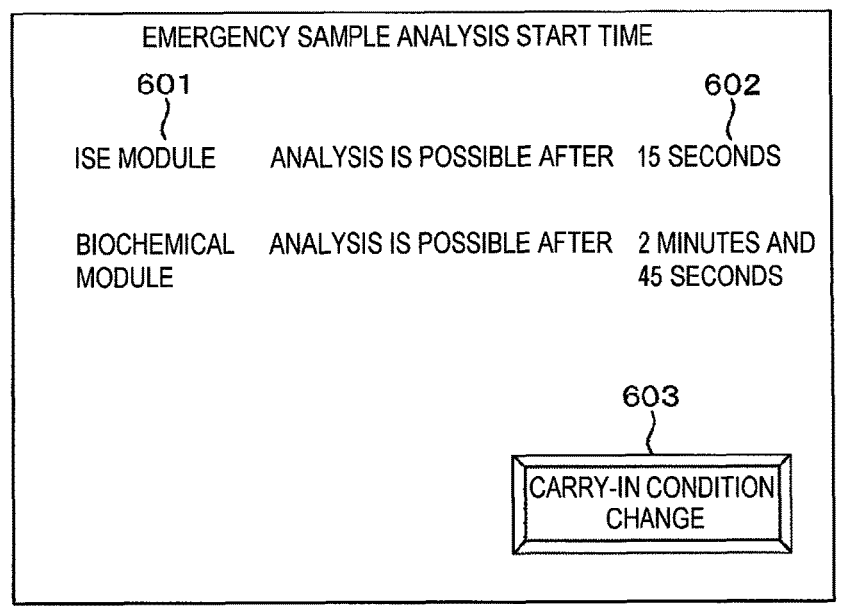
[FIG. 7]
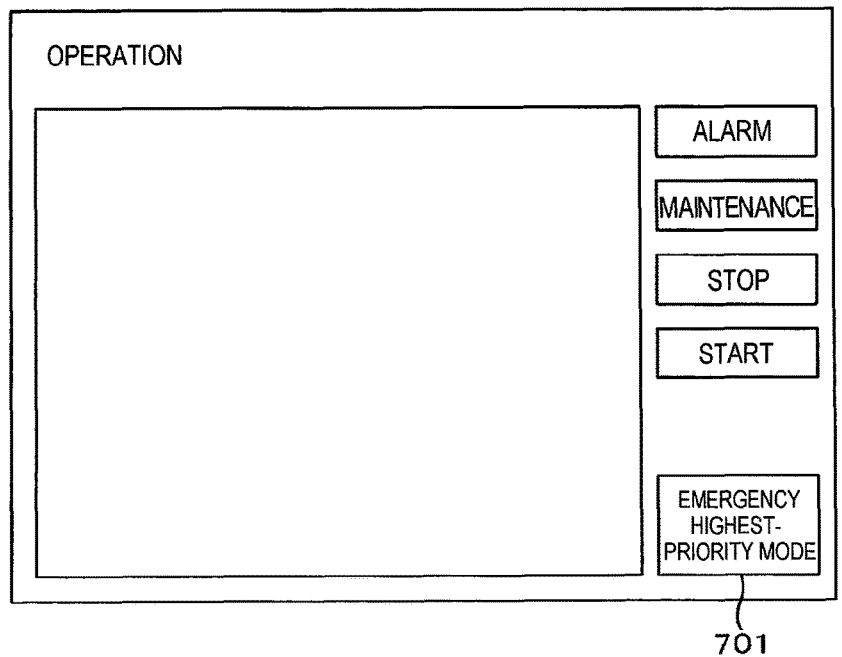

AUTOMATIC ANALYZER

TECHNICAL FIELD

The present invention relates to an automatic analyzer performing qualitative/quantitative analysis of biological samples such as blood and urine.

BACKGROUND ART

In an automatic analyzer including a means for installing samples in a rack and so on and conveying the samples to an analysis section, when emergency samples are installed in the analyzer, it is desired that the analysis is started in preference to samples of normal patients. In response to this, an automatic analyzer including a buffer for evacuating samples waiting for analysis is known, in which samples waiting for analysis are evacuated to the buffer when the rack in which the emergency samples are loaded is inputted, thereby preferentially starting the analysis of the emergency sample rack in preference to racks in the buffer.

When the distance from the buffer to a sample dispensing position is long, it is common that plural racks are conveyed on a conveyance path from the buffer to the sample dispensing position so as to sequentially analyze samples. However, when many racks exist on the conveyance path to the sample dispensing position in the case where the emergency sample rack is inputted, the analysis of the emergency samples are started after all samples on the conveyance path are analyzed, therefore, the analysis of the emergency samples will be delayed. In order to preferentially convey the emergency samples installed in the analyzer to the sample dispensing position, it is necessary to perform processing of returning plural racks in which samples have not been dispensed to the buffer again.

However, the same route is used for carrying-in and carrying-out in the automatic analyzer in which the buffer and the sample dispensing position are connected by one route, therefore, a waiting time occurs in the control of returning the racks to the buffer in the case where any of transfer controls in rack transfer from a rack input section to the buffer, rack transfer from the buffer to a rack storage section and rack transfer from the butter to the sample dispensing position overlaps the timing of rack transfer from the sample dispensing position to the buffer. In particular, in the automatic analyzer in which racks are conveyed from one buffer to plural different analysis sections, the rack transfer control between the buffer and the sample dispensing position is increased, therefore, it is highly likely that racks in a standby state in which samples have not been dispensed are difficult to immediately return to the buffer even when the emergency sample rack is inputted.

In response to the above, in a sample conveying system for processing samples before being analyzed by the analyzer, there is disclosed, in PTL 1, a method of limiting the number of racks to be carried in when the racks inputted into the system are conveyed to the conveyance path for immediately starting the processing of emergency samples.

CITATION LIST

Patent Literature

PTL 1: Japanese Patent No. 3760800

SUMMARY OF INVENTION

Technical Problem

The sample conveyance system described in PTL 1 performs given processing such as centrifugation, stopper opening, dispensing and stopper closing with respect to samples inputted to the system. Accordingly, variations of time necessary for processing of respective samples are small, therefore, a period of time until starting the processing of the emergency samples can fall into a certain time range by limiting the number of samples to be carried-in.

However, in the case of an automatic analyzer performing analysis items requested for respective samples or an automatic analysis system connecting plural automatic analyzers by conveyance lines, the number of analysis items requested for respective samples differs, therefore, periods of time taken until the dispensing of all samples loaded on one rack is completed are all different. That is, when many analysis items are requested for a certain sample, it is necessary to dispense the sample to the same number of reaction containers as the number of analysis items requested for the sample, therefore, a long period time is necessary from the start of dispensing to the end of dispensing when compared with a sample with a smaller number of requested analysis items. Accordingly, even when the number of racks to be carried-in to the analysis section is limited, there is a case where the necessary time until the completion of dispensing is not shortened consequently depending on the number of items requested for samples in the rack.

In a method of limiting the number of racks to be carried-in, a significant delay may occur in a result report of the emergency rack in which a rapid report of the analysis result is necessary.

The invention has been made in view of the above, and an object of the invention is to provide an automatic analyzer capable of conveying emergency samples to an analysis device and starting analysis of emergency samples immediately and efficiently without replacing racks when emergency samples are installed in the analyzer.

Solution to Problem

A typical structure of the invention for achieving the above object is as follows.

That is, an automatic analyzer includes an input section to which sample containers containing samples are inputted, a storage means for storing analysis items or the number of analysis items requested for respective samples, a sample processing section having a nozzle sucking part of the samples to be discharged to other containers in accordance with the analysis items or the number of analysis items stored in the storage means, and a conveyance means for conveying the sample containers to a suction position by the nozzle, in which the conveyance means, when new samples are inputted to the input section, controls conveyance of the new samples based on the number of analysis items in which suction by the nozzle has not been completed (the number of remaining analysis items) in analysis items requested for other samples scheduled to be dispensed before the new samples.

According to another structure of invention, there is provided an automatic analyzer including an input section to which sample containers containing samples are inputted, a storage means for storing analysis items or the number of analysis items requested for respective samples, a sample processing section having a nozzle sucking part of the samples to be discharged to other containers in accordance with the analysis items or the number of analysis items stored in the storage means, a buffer holding sample containers inputted to the input section before being conveyed to the sample processing section, and a conveyance means for conveying the sample containers held in the buffer to the sample processing section, in which the number of items which can be conveyed to the sample processing section is stored in the storage unit, and the conveyance means preferentially conveys to the sample processing section sample containers with higher priority in sample containers held in the buffer when the number of analysis items in which suction by the nozzle has not been completed (the number of remaining analysis items) is smaller than the number of items which can be conveyed.

Advantageous Effects of Invention

According to the above means, it is possible to convey analysis items to an analysis unit immediately and efficiently without controlling replacement of racks even when emergency samples are newly inputted.

As the number of analysis items requested for samples in a waiting state for analysis in the analysis section can be constantly limited to be smaller than a fixed number, a period of time until a measurement result of emergency samples is outputted can be reduced even when emergency samples are newly inputted.

BRIEF DESCRIPTION OF DRAWINGS

FIG. 1 is a view schematically showing the overall structure of an automatic analyzer according to one embodiment of the invention.

FIG. 2 is a processing flow for conveying emergency samples preferentially to an analysis section.

FIG. 3 is a configuration diagram of software performing a process of determining whether samples can be conveyed to the analysis section.

FIG. 4 shows an example of a screen for setting and changing the number of items which can be carried-in.

FIG. 5 shows an example of a screen for setting a rule for conveying racks from a buffer to the analysis section.

FIG. 6 shows an example of a screen displaying predicted times at which sample dispensing is started.

FIG. 7 shows an example of a screen for instructing transfer of racks to be temporarily stopped when the analysis of emergency samples is started.

DESCRIPTION OF EMBODIMENTS

Hereinafter, an embodiment of the invention will be explained with reference to the drawings. The present embodiment is a mode for carrying out the invention, and the invention is not limited to the embodiment.

FIG. 1 is a view schematically showing the overall structure of an automatic analyzer according to one embodiment of the invention. In FIG. 1, the automatic analyzer includes sample racks 111 in which plural sample containers containing biological samples such as blood and urine (hereinafter referred to as samples) are housed, a carry-in section 101 in which the sample racks 111 are installed, a conveyance line 102 for conveying the sample racks 111, a buffer 104 holding conveyed plural racks, an analysis section 105 analyzing samples conveyed from the buffer through a conveyer line 106 by using a suction nozzle and a storage section 103 storing the sample racks 111 the analysis of which has been completed.

The analysis section 105 includes a reaction disk 108 having plural reaction containers, a sample dispensing probe 107 dispensing samples to the reaction containers in the reaction disk 108 from sample containers by rotational drive or vertical drive, a reagent disk 110 on which plural reagents are installed, reagent dispensing nozzles 109 dispensing reagents from reagent bottles in the reagent disk 110 to the reaction containers in the reaction disk 108 and a wash mechanism 112 washing the reaction containers.

The sample racks 111 are installed in the carry-in section 101 or an emergency rack input entrance 113, which are carried into the buffer 104 which can be randomly accessed by the conveyance line 102. The automatic analyzer carries the rack with the highest priority in the racks stored in the buffer 104 into the analysis section 105 by the conveyer line 106 in accordance with rules of the priority defined according to types of racks. For example, when a general rack and an emergency rack are both stored in the buffer 104, the emergency rack with higher priority will be conveyed.

The rack arrived at the analysis section 105 is further transferred to the sample dispensing position, and the sample is dispensed into the reaction containers in the reaction disk 108 by the sample dispensing probe 107. The sample dispensing probe 107 dispenses the sample for the necessary number of times in accordance with analysis items requested for the sample.

The sample dispensing probe 107 dispenses the samples with respect to all sample containers loaded on the rack, and the rack in which dispensing processing has been completed with respect to all sample containers is transferred to the buffer 104 again. The rack in which all sample dispensing processing including automatic recheck has been completed is transferred to the storage section 103. Instructions for analysis as well as confirmation for analysis results or the analyzer status are performed by an input/output section 114.

The structure shown in FIG. 1 is one embodiment of the invention. It is also preferable to apply a structure in which the sample dispensing probe 107 sucks the samples on the conveyance line 102 without providing the conveyer line 106. It is further preferable to provide a return line for conveying the sample rack in which the sample dispensing has been completed to the buffer 104 or the storage section 103 separately from the conveyance line 102.

It is also preferable to convey the sample rack 111 inputted to the carry-in section 101 directly to the analysis section 105 without providing the buffer 104. Moreover, a structure in which plural analysis sections are connected by the conveyer line may be applied. In this case, buffers 104 corresponding to respective analysis sections may be provided as well as one buffer 104 can be shared among plural number of analysis sections. Furthermore, it is preferable to convey the sample rack 111 from the carry-in section 101 directly to respective analysis sections without providing the buffer 104.

Although the case where the rack in which plural sample containers can be loaded is used as the sample rack 111 has been explained in the embodiment, the invention is not limited to this, and a type of the rack in which only one sample container can be loaded can be also used.

Next, a means for conveying the emergency rack immediately to the analysis section when the emergency rack is installed will be explained.

FIG. 2 shows an example of processing for conveying emergency samples preferentially to the analysis section by a flowchart.

First, when the automatic analyzer recognizes an input of the emergency rack, transfer of a new rack from the buffer 104 to the analysis section 105 is temporarily stopped for transferring emergency samples immediately to the buffer 104. In order to realize this, first, whether the automatic analyzer recognizes the emergency samples or not is checked in a process of determining existence of emergency samples 201. For recognition of the input of the emergency rack, for example, a sensor 115 for detecting an installation of the rack at the emergency rack input entrance 113, a barcode reader disposed at the position of the sensor 115 for reading a barcode of the emergency rack or a function for detecting an input of a request for analyzing emergency samples into the analyzer is enumerated.

When the automatic analyzer recognizes the emergency sample in the process of determining existence of emergency samples 201, whether conveyance of the rack from the emergency rack input entrance 113 to the buffer 104 can be controlled or not is determined in a process of determining whether buffer control is possible or not 202. When the emergency rack can be conveyed to the buffer, the emergency rack is transferred to the buffer 104 in a process of conveying an emergency rack 203. When it is difficult to convey the emergency rack from the emergency rack input entrance 113 to the buffer 104, for example, when another rack is already being transferred, the processing of conveying the emergency rack is stopped once, and the process of determining whether buffer control is possible or not 202 is performed again after waiting until the conveyance of the rack during conveyance is finished and the transfer control to the buffer 104 becomes possible.

On the other hand, when the automatic analyzer does not recognize the emergency rack in the process of determining existence of emergency samples 201, whether the rack which can be supplied to the analysis section 105 exists in the buffer 104 or not is checked (a process of determining whether sample supply to the analysis section is necessary or not 204) as it is not necessary to stop the conveyance control of the buffer 104 for emergency samples. The rack which can be supplied to the analysis section is a rack on which samples in which any of measurements in the analysis section 105 has not been completed are loaded, which corresponds to any of the emergency rack, the general rack, an accuracy management rack and a standard sample rack. Moreover, racks in the standby state in the buffer 104 for automatic recheck after all the measurements has been completed in the analysis section 105 are also included.

When it is determined that there exists the rack which can be supplied to the analysis section 105 in the process of determining whether sample supply to the analysis section is necessary or not 204, whether the rack transfer to the analysis 105 can be controlled or not is determined in a process of determining whether transfer control to the analysis section is possible or not 205. Whether the conveyance to the analysis section is possible or not is determined depending on the existence of the rack at the entrance of the conveyer line 106 and whether the carry-in to the conveyer line 106 is possible or not. For example, the control of conveying the rack from the buffer 104 to the conveyer line is determined to be possible in the case where a rack sensor installed at the entrance of the conveyer line 106 is in the OFF-state (namely, in the case where there is no rack in the entrance of the conveyer line 106) as well as a motor of the conveyer line is stopped.

When it is determined that the transfer to the analysis section is possible in the process of determining whether transfer control to the analysis section is possible or not 205, a process of determining the number of remaining analysis items 206 is performed. When the number of remaining analysis items is equal to or smaller than the number of items which can be carried-in, the rack is transferred to the analysis section 105 in a process of controlling transfer to an analysis section 207.

Here, the number of items which can be carried-in is a value predetermined in the setting by an operator or in the default setting, which indicates the number of analysis items which can be processed by the analysis section to a degree in which the conveyance line of the automatic analysis system is not jammed.

"To a degree in which the conveyance line is not jammed" means to avoid a state in which the conveyance line is substantially difficult to use as plural sample racks 111 continuously exist on the conveyance line as well as to avoid a state in which the total number of analysis items requested for the samples on the conveyance line 102 and the conveyer line 106 will be excessive as compared with a processing ability of the sample dispensing probe 107 in the analysis section 105. Furthermore, the above degree means a state in which a period of time necessary for obtaining an analysis result of newly-inputted emergency samples is within a given period of time.

Though the number of items which can be carried-in may be determined by default and may be set by an operator, it is preferable that the number is set in accordance with an allowable waiting time of the emergency sample. For example, when it is desired to know the analysis result at least after a time "m" passes from the input of emergency samples, it is necessary to start dispensing the emergency samples after a time (m−t) obtained by subtracting a time "t" necessary for the analysis passes. Accordingly, when a period of time necessary for dispensing the sample once by the sample dispensing probe is a time "s", the number of items which can be carried-in is set to (m−t)/s or a value close to this.

That is, in the present embodiment, samples existing on a path from a sample input section to the sample dispensing probe (including the buffer and the conveyance line) are managed and permission/inhibition control of conveying next samples to the analysis section is performed based on the number of analysis items requested for the samples.

The number of remaining analysis items is the number of items in which sample dispensing has not been completed in the analysis section 105 in the samples on the rack existing in the conveyer line 106 of each analysis section 105. For example, in the case where one rack on which five sample containers can be loaded exists in the conveyer line 106, 6 items are requested for a sample at a position 1, 1 item is requested for a sample at a position 2, 2 items are requested for a sample at a position 3, 10 items are requested for a sample at a position 4 and 3 items are requested for a sample at a position 5, and when all the dispensing of the samples at the position 2 has been already completed, the number of remaining analysis items will be 15 items which is the total number of items requested for the samples existing at positions 3 to 5.

When it is determined that there are plural racks which can be supplied to the analysis section 105 in the process of determining whether sample supply to the analysis section is necessary or not 204, one rack to be supplied is determined according to the predetermined order of priority of samples. For example, when both the emergency rack and the general rack exist, the emergency rack is preferentially conveyed. Even in the emergency racks, both an emergency rack of recheck and an emergency rack of the first time exist, the emergency rack of recheck is preferentially conveyed. In this case, the order of priority becomes high in the order of the rack of the emergency samples of recheck, the rack of the emergency samples of the first time and the rack of the common samples. When plural emergency racks exist, the rack in which the time of sample recognition is the earliest is preferentially conveyed. According to the process, analysis of automatic recheck is performed in preference to the analysis of the first time even when both racks are emergency racks. When the determined rack has the highest priority, the process of controlling transfer to the analysis section 207 may be performed not depending on the process of determining the number of remaining analysis items 206. For example, in the case where the emergency samples of automatic recheck is determined to be priority 1 and the emergency samples of the first time is determined to be priority 2, the rack is immediately conveyed to the analysis section 105 in the case of the emergency samples of automatic recheck, but the rack of the emergency samples of the first time is transferred to the analysis section 105 after the condition of the process of determining the number of remaining analysis items 206 holds in consideration of occurrence of automatic recheck of emergency samples during a period until the condition of the process of determining the number of remaining analysis items 206 holds.

When the transfer to the analysis section is determined to be difficult in the process of determining whether transfer control to the analysis section is possible or not 205, the supply of racks from the buffer 104 to the analysis section 105 is stopped, and the racks are allowed to be waited inside the buffer 104. In the case of the analyzer including lines through which the racks are transferred from one buffer 104 to plural analysis sections 105, the process of determining whether transfer control to the analysis section is possible or not 205 is performed respectively in other analysis sections, and when there exists the analysis section to which the rack can be transferred, the rack is transferred to the analysis section.

When it is determined that there is no rack which can be supplied to the analysis section 105 inside the buffer 104 in the process of determining whether sample supply to the analysis section is necessary or not 204, whether there is a rack which can be received from the analysis section 105, namely, whether there is a rack in which all sample dispensing processing in the analysis section 105 has been completed or not is checked in a process of determining existence of a sample-dispensing completed rack 208.

When it is determined that there is a rack which can be received from the analysis section 105 in the process of determining existence of the sample-dispensing completed rack 208, in the case where the rack control from the analysis section 105 to the buffer 104 is possible in a process of determining whether buffer transfer control is possible or not 209, the rack is conveyed from the analysis section 105 to the buffer in a process of controlling buffer transfer 210.

When the rack conveyance from the analysis section 105 to the buffer 104 is determined to be difficult in the process of determining whether buffer transfer control is possible or not 209, racks in which all the sample dispensing processing has been completed wait in the conveyer line.

The automatic analyzer executes the above processing at regular time intervals. For example, when the transfer to the analysis section is determined to be difficult in the process of determining whether transfer control to the analysis section is possible or not 205, in the case where the sample dispensing processing in the analysis section 105 proceeds, the relation of "the number of remaining analysis items is equal to or smaller than the number of items which can be carried-in holds, and the rack conveyance to the analysis section 105 can be performed. Additionally, in the case where the rack conveyance from the analysis section 105 to the buffer 104 is determined to be difficult in the process of determining whether buffer transfer control is possible or not 209, when the control of the buffer 104 ends and the conveyance control to the buffer 104 becomes possible, the rack in which all sample dispensing processing has been completed can be conveyed from the analysis section 105 to the buffer 104.

There exists an automatic analyzer which can perform the rack transfer from the analysis section 105 to the buffer 104 and the rack transfer from the buffer 104 to the analysis section 105 continuously. In such automatic analyzer, a replacement process of racks may be performed by adding a condition that the process of determining whether sample supply to the analysis section is necessary or not 204 and the process of determining existence of a sample-dispensing completed rack 208 hold at the same time.

In the case where plural analysis sections are connected to one buffer 104, whether there exists a corresponding rack may be checked from the analysis section with the highest priority in accordance with the predetermined priority of the analysis sections in the processing of determining whether sample supply to the analysis section is necessary or not 204 and the process of determining existence of a sample-dispensing completed rack 208.

The case where the automatic analyzer recognizes emergency samples in the process of determining existence of emergency samples 201 may include a case where a request for analyzing emergency samples arrives at the automatic analyzer in addition to the case where the automatic analyzer detects the emergency rack by the sensor.

Furthermore, there exists an automatic analyzer including the line through which racks are supplied to the analysis section and the line through which the racks are returned from the analysis section separately. In this case, the process of determining existence of a sample-dispensing completed rack 208 may be executed to thereby perform control of the line through which the racks are returned from the analysis section 105 to the buffer 104 at the same time even when emergency samples are recognized or there exists a rack which can be supplied to the analysis section 105 in the process of determining existence of emergency samples 201 or the process of determining whether sample supply to the analysis section is necessary or not 204.

FIG. 3 is a view showing an example of a software configuration performing processing of determining whether racks can be conveyed to the analysis section in the process of determining whether sample supply to the analysis section is necessary or not 204, the process of determining whether transfer control to the analysis section is possible or not 205 and the process of determining the number of remaining analysis items 206, and performing processing of determining whether the rack can be conveyed from the analysis section in the process of determining existence of the sample-dispensing completed rack 208 and the process of determining whether buffer transfer control is possible or not 209. These determination processes are performed by a conveyance control unit 304.

A parameter management unit 301 includes a conveyance parameter table which stores information of the number of items which can be carried-in with respect to the analysis section.

When the number of items which can be carried-in is large, the possibility that emergency samples are not rapidly processed is increased, and when the number of items which can be carried-in is extremely small, there is the possibility that the continuous sample processing may be difficult to be performed. The value may be set by default so as to correspond to the processing ability of the analysis section as well as may be inputted by the operator oneself. In the system in which plural analysis sections are installed along the conveyance path, it is desired that the parameter management unit 301 can set the number of items which can be carried-in as the conveyance parameter with respect to each analysis section as the processing ability may differ according to the analysis sections.

The parameter management unit 301 sets the number of emergency slots as a conveyance parameter. The number of emergency slots is the number of slots in which only the emergency racks can be installed in the buffer. When the number of slots is more than a fixed number, the processing of conveying the racks from the emergency rack input entrance to the buffer can be preferentially performed, therefore, samples of the emergency rack can be continuously analyzed in preference to general racks waiting for analysis. The value can be determined according to the structure of the analyzer as well as can be inputted by the user.

A conveyance planning unit 302 includes a conveyance status table managing information of racks inside the buffer 104 and racks currently being conveyed from the buffer 104 to the analysis section 105, which stores at least numbers of racks for identifying the racks, the numbers of analysis items requested for respective samples installed in the rack, priorities defined according to respective carry-in/carry-out destinations and the status of racks.

The status of the racks includes Waiting for carry-in: a state where the rack is waiting for conveyance to the analysis section in the buffer, During carry-in: a state where the rack exists in the path from the buffer to the analysis section, Waiting for carry-out: a state where the rack is waiting for conveyance from the buffer to the storage section, Sample dispensing completion: a state where the rack is waiting in the analysis section for returning the rack in which sample dispensing has been completed from the analysis section to the buffer, Standby: a state where the analysis section as the conveyance destination is not determined in the rack carried-in to the buffer or a state where automatic recheck has not been decided in the rack in which sample dispensing has been completed and other states.

An analysis planning unit 303 includes an analysis status table, which stores numbers of samples for identifying samples, item codes indicating the analysis items requested for respective samples and the status of the analysis concerning samples in the rack inputted into the automatic analyzer or the automatic analysis system.

The status of the analysis is sorted out into states necessary for calculating at least the number of remaining analysis items such as Not started: a state where measurement of the analysis item is not started, During analysis: a state where sample dispensing of the analysis item is performed and before a measurement result is outputted and Completion: a state where the report of the analysis result has been completed.

In the system in which plural analysis sections are installed along the conveyance path, it is desirable that the analysis planning unit 303 can set the number of items which can be carried-in as the conveyance parameter with respect to each analysis section as the processing ability may differ according to the analysis sections.

When at least one rack with the status of "Waiting for carry-in" exists in the racks stored in the conveyance status table, the conveyance planning unit 302 inquires of the analysis planning unit 303 whether the rack can be carried in or not. The analysis planning unit 303 refers to the number of items to be carried-in in the parameter management unit 301 and counts up the number of items the status of which is "not started" (the number of remaining analysis items) in item information stored in the analysis status table, then, makes a reply of "carry-in is allowed" with respect to the inquiry for the possibility of carry-in from the conveyance planning unit 302 when the value is lower than the number of items which can be carried-in.

In the case where there are plural sample dispensing positions in the analysis section 105, it is preferable that the analysis planning unit 303 counts up samples the status of which is "not started" with respect to respective sample dispensing positions in the item codes stored in the analysis status table and compares the maximum number of samples with the number of items which can be carried-in of the parameter management unit 301 in respective sample dispensing positions.

When the conveyance planning unit 302 receives a reply of "carry-in is allowed" from the analysis planning unit 303, the conveyance control unit 304 performs control of the conveyance mechanism so as to convey the rack with the highest priority from the buffer to the analysis section in the racks the status of which is the "waiting for carry-in".

When the conveyance planning unit 302 receives a reply of "carry-in is not allowed" from the analysis planning unit 303, the rack transfer from the buffer to the analysis section is stopped.

The conveyance planning unit 302 performs control of the conveyance mechanism so as to convey the racks from the analysis section to the buffer in the case where "carry-in is not allowed" as well as there exists the sample rack with the status of "sample dispensing completion".

In the case where there is no sample rack with the status of "sample dispensing completion" as well as there exists the sample rack with the status of "waiting for carry-out", conveyance control from the buffer to the storage section is performed.

FIG. 4 shows an example of a screen for setting and changing the number of items which can be carried-in in the parameter management unit 301 as the condition of carrying the racks from the buffer 104 into the analysis section 105. A rack carry-in condition setting screen 401 is displayed on the input/output section, having an input area for the number of items which can be carried-in 402 to which the operator can input the number of items which can be carried-in as a value for allowing the rack to be carried-in from the buffer. On the screen, an OK button 403 and a cancel button 404 are provided, and when the OK button 403 is pressed down, the inputted number of items which can be carried-in is reflected on the conveyance parameter table of the parameter management unit 301.

The pressing of the OK button 403 is not limited to the case where the automatic analyzer is in the standby state. For example, when the number of items which can be carried-in is changed to a smaller value during analysis in the case where many emergency samples arrive, the value is reflected on the number of items which can be carried-in on the conveyance parameter table of the parameter management unit 301 at the time of changing the value, thereby changing the condition for allowing carry-in to the analysis section 105.

Although the means for setting the number of items which can be carried-in has been explained in the example of FIG. 4, it is also possible to apply a method of setting a period of time until all sample dispensing of unanalyzed items of samples in the analysis section is completed, not the number of items which can be carried-in. In that case, for example, a period of time until the sample dispensing is completed is calculated from the following (formula 1). A set value is previously set, and an obtained calculated value is compared with the set value. When the calculated value is equal to or lower than the set value, the carry-in may be permitted.

> (the number of non-dispensed items requested for samples in the analysis section+the number of times of washes for avoiding carry-over)×time necessary for one analysis cycle+time necessary for movement from the buffer to the dispensing position by the sample probe   (formula 1)

In the case where the time necessary for movement from the buffer to the dispensing position by the sample probe is sufficiently short, there is a case where it is not necessary to consider the "time necessary for movement from the buffer to the dispensing position by the sample probe" in the (formula 1).

Here, the analysis cycle indicates a period of time necessary for the sample dispensing probe 107 dispensing the samples from the sample containers on the sample rack 111 and discharging the samples into the reaction containers on the reaction disk 108, which is also a period of time necessary for the wash for avoiding carry-over.

The wash for avoiding carry-over means a washing operation performed before the sample dispensing probe 107 sucks the sample different from the sample which has been sucked last time.

Though the set value to be compared with the calculated value may be fixed by default as well as may be set by the operator, it is preferable to be set in accordance with an allowable wait time of the emergency samples. For example, in the case where the analysis result is desired to be known at least after a time "m" passes from the input of the emergency samples, it is necessary to start the dispensing of the emergency samples after a time (m−t) obtained by subtracting the time "t" necessary for analysis passes, therefore, the set value may be set to (m−t).

In the case of the system in which the sample racks are conveyed from one buffer 104 to plural analysis sections 105, or in the case where one system includes plural buffers 104 and plural analysis sections, the number of items which can be carried-in can be set with respect to respective analysis sections as the processing ability may differ according to respective analysis sections.

FIG. 5 shows an example of a screen for setting a rule of applying the means for conveying the racks from the buffer to the analysis section when the number of unanalyzed items in the analysis section is lower than the fixed value. A rack conveyance rule application setting screen 501 is displayed on the input/output section 114, having a time-slot input area 502. For example, the rule is desirable to be applied only to nighttime, 20:00 to 6:00 is inputted to the time-slot input area 502. On the screen, an OK button 503 and a cancel button 504 are provided, and when the OK button 503 is pressed down, the means for conveying the new rack from the buffer to the analysis section is applied in the case where the number of unanalyzed items is lower than the fixed value during the inputted time slot.

In the example, the analysis planning unit 303 may refer to the number of items which can be carried-in in the parameter management unit 301 as the number of items which can be carried-in during the period of 20:00 to 6:00 and may apply the default value during time slots other than the above time slot. Though only one time slot can be set in the drawing, it is also preferable to set the number of items which can be carried-in in plural time slots in consideration of round-the-clock operation.

FIG. 6 shows an example of a screen displaying predicted times at which sample dispensing is started when the emergency samples are inputted at present. The screen is included in a screen displaying the present status of the analyzer such as overview on the input/output section 114, displaying a name display area 601 of respective analysis sections and predicted values 602 of time at which the emergency rack inputted at present reaches the sample dispensing position of each analysis sections.

The predicted value 602 of time at which the rack reaches the sample dispensing position of each analysis section is calculated by, for example, the following (formula 2) and displayed on the input/output section.

> Movement time from the emergency sample input entrance to the buffer+(the number of non-dispensed items requested for samples in the analysis section+the number of times of washes for avoiding carry-over)×time necessary for one analysis cycle+movement time from the buffer to the dispensing position   (formula 2)

Here, the definition of the analysis cycle and the number of times of washes for avoiding carry-over are the same as the (formula 1). Additionally, when the time necessary for movement from the buffer to the dispensing position by the sample probe is sufficiently short, there is a case where it is not necessary to consider the "time necessary for movement from the buffer to the dispensing position by the sample probe" in the same manner as the (formula 1).

The screen has a carry-in condition change button 603. After the user checks the predicted value 602 of the time at which the rack reaches the sample dispensing position of each analysis section, when the start of analysis of the emergency samples is desired to be performed earlier, rack carry-in condition setting screen 401 is displayed by pressing down the carry-in condition change button 603. The screen may display the predicted time until the analysis result of the emergency samples is obtained. That is because the time at which the analysis result is obtained depends on the time during which the sample dispensing processing is performed.

FIG. 7 shows an example of a screen for instructing transfer of the rack in the path from the emergency rack input entrance 113 to the analysis section 105 to be temporarily stopped when the analysis of the emergency samples is started during the operation.

An emergency highest-priority mode button 701 is provided, for example, in a constant display area at which the user can instruct stop/start in the input/output section 114.

When the emergency highest-priority mode button 701 is pressed down, carry-in of racks other than emergency samples from the buffer 104 to the analysis section 105 and supply of new racks from the carry-in section 101 are stopped to thereby secure the path from the emergency rack input entrance 113 to the analysis section 105, as a result, the rack can be immediately conveyed to the analysis section 105 in the case where the emergency samples are installed at the emergency rack input entrance. As methods of ending the emergency highest priority mode, there are, for example, a method of pressing down the emergency highest-priority mode button 701 again, a method of completing recognition of emergency racks and so on.

Furthermore, it is possible to apply a method in which the carry-in from the buffer 104 to the analysis section 105 of all racks including the emergency rack already stored in the buffer section is suspended when the emergency highest-priority mode button 701 is pressed down to thereby give the highest priority to emergency samples to be inputted next.

According to the above, when the number of remaining analysis items of samples in the analysis section is lower than the set value, racks are transferred from the buffer 104 to the analysis section 105, thereby limiting the transfer of racks other than the emergency rack and improving the priority of conveying the emergency rack, as a result, analysis of the emergency rack can be preferentially performed. Additionally, the means for temporarily stopping the transfer of racks in the path from the emergency rack input entrance 113 to the analysis section 105 at the time of recognizing the emergency samples is provided, thereby allowing the analysis of the emergency rack to be started further earlier. It is not always necessary to provide the emergency highest-priority mode button 701, and this function may be provided in a sample stop key.

It is not always necessary that plural sample containers are installed in the rack, though not explained in the embodiment. For example, the technique of the invention can be applied to a case where only one sample container is loaded in the rack.

REFERENCE SIGNS LIST

101 carry-in section
102 conveyance line
103 storage section
104 buffer
105 analysis section
106 conveyer line
107 sample dispensing probe
108 reaction disk
109 reagent dispensing nozzle
110 reagent disk
111 sample rack
112 wash mechanism
113 emergency rack input entrance
114 input/output section
201 process of determining existence of emergency samples
202 process of determining whether buffer control is possible or not
203 process of conveying an emergency rack
204 process of determining whether sample supply to the analysis section is necessary or not
205 process of determining whether transfer control to the analysis section is possible or not
206 process of determining the number of remaining analysis items
207 process of controlling transfer to an analysis section
208 process of determining existence of a sample-dispensing completed rack
209 process of determining whether buffer transfer control is possible or not
210 process of controlling buffer transfer
301 parameter management unit
302 conveyance planning unit
303 analysis planning unit
304 conveyance control unit
401 rack carry-in condition setting screen
402 input area for the number of items which can be carried-in
403, 503 OK button
404, 504 cancel button
501 rack conveyance rule application setting screen
502 time-slot input area
601 name display area of respective analysis sections
602 predicted value of time at which the rack reaches the sample dispensing position of each analysis section
603 carry-in condition change button
701 emergency highest-priority mode button

The invention claimed is:

1. An automatic analyzer comprising:
a carry-in section in which one or more sample containers of a plurality of sample containers containing samples are loaded;
an emergency sample container input entrance that is connected to a conveyance line and to which emergency sample containers containing emergency samples are loaded;
a sensor configured to detect an input of an emergency sample container to the emergency sample container input entrance;
a buffer comprised of a plurality of slots, each slot is configured to hold one or more sample containers off the conveyance line which have been loaded in the carry-in section and conveyed to the buffer from the carry-in section, the plurality of slots configured to hold emergency sample containers input from the emergency sample container input entrance and sample containers input from the carry-in section;
a sample analysis section, including a reagent disk, a reaction disk holding a plurality of reaction containers, and a sample dispensing probe configured to suction a sample from a sample container at a suction position and dispense the sample into a first reaction container on the reaction disk; and
a control unit with an input and coupled to each of the conveyance line, the sensor, and the sample dispensing probe,
wherein the conveyance line is connected to the carry-in section and the buffer and extends from and is configured to carry sample containers from the carry in section and the emergency sample entrance to the buffer and to the sample analysis section and is configured to convey one or more sample containers held in the buffer to the suction position of the sample dispensing probe, and
wherein the control unit is programmed to:
receive and store an input to change a predetermined number of analysis items of samples permitted to be on the conveyance line, which is based on a sample processing rate of the sample analysis section,
receive and store an input to change a predetermined number indicating a number of slots of the buffer used only for emergency sample containers to be input into the emergency sample container input entrance,
store a number of analysis items that are to be analyzed for each sample on the conveyance line,
control the sample dispensing probe to suction and dispense a sample from a sample container at the suction position a number of times that is in correspondence with the number of analysis items to be analyzed for the sample in the sample container at the suction position, identify, based on the detection of the sensor, an emergency sample container in an emergency rack that has been input into the emergency sample container input entrance, input and store a time slot indicating a period of time during which the control unit determines a current number of analysis items on the conveyance line for which the sample dispensing probe has not suctioned and dispensed a sample from a sample container at the sample suction position, determine whether a current time is within the time slot and upon determining the current time is within the input time slot determine the current number of analysis items on the conveyance line for which the sample dispensing probe has not suctioned and dispensed a sample, determine whether the current number of analysis items on the conveyance line for which the probe has not suctioned and dispensed a sample is less than the predetermined number of analysis items permitted to be on the conveyance line, upon determining the current number of analysis items on the conveyance line for which the probe has not suctioned and dispensed a sample is less than the predetermined number of analysis items permitted to be on the conveyance line, control the conveyance line to convey all of the emergency sample containers held in the slots of the buffer before conveying any other sample container from the buffer to the suction position.

2. The automatic analyzer according to claim 1, wherein the control unit is programmed to control the conveyance line to convey the emergency sample containers in preference to another sample container that has been loaded in the carry-in section upon receiving, by the control unit, a request to analyze the emergency samples or the sensor detects an input of an emergency sample container.

3. The automatic analyzer according to claim 2, further comprising:
a display, coupled to the control unit,
wherein the control unit is programmed to display a predicted time until the emergency samples are suctioned by the sample dispensing probe.

4. An automatic analyzer comprising:
a carry-in section in which one or more sample containers of a plurality of sample containers containing samples are loaded;
an emergency sample container input entrance that is connected to a conveyance line and to which emergency sample containers containing emergency samples are loaded; and
a barcode reader configured to read barcode information upon input of an emergency sample container to the emergency sample container input entrance;
a buffer comprised of a plurality of slots, each slot is configured to hold one or more sample containers off the conveyance line which have been loaded in the carry-in section and conveyed to the buffer from the carry-in section, the plurality of slots configured to hold emergency sample containers input from the emergency sample container input entrance and sample containers input from the carry-in section;
a sample analysis section, including a reagent disk, a reaction disk holding a plurality of reaction containers, and a sample dispensing probe configured to suction a sample from a sample container at a suction position and dispense the sample into a first reaction container on the reaction disk; and
a control unit with an input and coupled to each of the conveyance line, the barcode reader, and the sample dispensing probe,
wherein the conveyance line is connected to the carry-in section and the buffer and extends from and is configured to carry sample containers from the carry in section and the emergency sample entrance to the buffer and to the sample analysis section and is configured to convey one or more sample containers held in the buffer to the suction position of the sample dispensing probe, and
wherein the control unit is programmed to:
receive and store an input to change a predetermined number of analysis items of samples permitted to be on the conveyance line, which is based on a sample processing rate of the sample analysis section,
receive and store an input to change a predetermined number indicating a number of slots of the buffer used only for emergency sample containers to be input into the emergency sample container input entrance,
store a number of analysis items that are to be analyzed for each sample on the conveyance line,
control the sample dispensing probe to suction and dispense a sample from a sample container at the suction position a number of times that is in correspondence with the number of analysis items to be analyzed for the sample in the sample container at the suction position,
identify, based on the barcode information read by the barcode reader, an emergency sample container in an emergency rack that has been input into the emergency sample container input entrance,
input and store a time slot indicating a period of time during which the control unit determines a current number of analysis items on the conveyance line for which the sample dispensing probe has not suctioned and dispensed a sample from a sample container at the sample suction position,
determine whether a current time is within the time slot and upon determining the current time is within the input time slot determine the current number of analysis items on the conveyance line for which the sample dispensing probe has not suctioned and dispensed a sample,
determine whether the current number of analysis items on the conveyance line for which the probe has not suctioned and dispensed a sample is less than the predetermined number of analysis items permitted to be on the conveyance line,
upon determining the current number of analysis items on the conveyance line for which the probe has not suctioned and dispensed a sample is less than the predetermined number of analysis items permitted to be on the conveyance line, control the conveyance line to convey all of the emergency sample containers held in the slots of the buffer before conveying any other sample container from the buffer to the suction position.

* * * * *